(12) United States Patent
Lem

(10) Patent No.: US 8,911,716 B2
(45) Date of Patent: Dec. 16, 2014

(54) SAFFRON ODORANTS

(75) Inventor: George Lem, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/005,763

(22) PCT Filed: Feb. 20, 2012

(86) PCT No.: PCT/EP2012/052871
§ 371 (c)(1),
(2), (4) Date: Sep. 17, 2013

(87) PCT Pub. No.: WO2012/126686
PCT Pub. Date: Sep. 27, 2012

(65) Prior Publication Data
US 2014/0010774 A1 Jan. 9, 2014

(30) Foreign Application Priority Data
Mar. 18, 2011 (EP) .................................... 11158871

(51) Int. Cl.
| | | |
|---|---|---|
| *C11B 9/00* | (2006.01) | |
| *A61L 9/01* | (2006.01) | |
| *C11D 3/50* | (2006.01) | |
| *C11D 9/44* | (2006.01) | |
| *A61K 8/33* | (2006.01) | |
| *A61K 8/49* | (2006.01) | |
| *A61Q 13/00* | (2006.01) | |
| *C07C 403/16* | (2006.01) | |
| *C07C 49/21* | (2006.01) | |

(52) U.S. Cl.
CPC ............. *C11B 9/0034* (2013.01); *C07C 403/16* (2013.01); *C07C 49/21* (2013.01); *C07C 2101/16* (2013.01)
USPC ........... 424/65; 568/377; 424/70.1; 424/76.2; 514/772; 512/22; 512/11; 512/13; 512/6; 512/24; 510/106; 510/103

(58) Field of Classification Search
USPC ............. 424/65, 70.1, 76.2; 514/772; 512/22, 512/11, 13, 6, 24; 510/106, 103; 568/377
See application file for complete search history.

(56) References Cited

U.S. PATENT DOCUMENTS

| | | |
|---|---|---|
| 3,872,031 A | 3/1975 | Mookherjee et al. |
| 5,485,251 A | 1/1996 | Kita et al. |
| 6,177,400 B1 * | 1/2001 | Mimoun et al. ................ 512/24 |

FOREIGN PATENT DOCUMENTS

| | | |
|---|---|---|
| EP | 955290 A1 | 11/1999 |
| EP | 1791934 A1 | 6/2007 |
| JP | 1995121015 A | 5/1995 |
| WO | WO 98/50010 A1 | 11/1998 |
| WO | WO 2008/026140 A2 | 3/2008 |

OTHER PUBLICATIONS

International Search Report and Written Opinion, application PCT/EP2012/052871, mailed Apr. 17, 2013.
Sell C. S., Angew. Chemie, Int. Ed. 2006, vol. 45, n° 38, pp. 6254-6261.

* cited by examiner

*Primary Examiner* — Ernst V Arnold
*Assistant Examiner* — Hong Yu
(74) *Attorney, Agent, or Firm* — Winston & Strawn LLP

(57) ABSTRACT

The present invention concerns a compound of formula (I), in the form of any one of its stereoisomers or a mixture thereof, and wherein the dotted line represents a carbon-carbon single or double bond; as well as its use as perfuming ingredient.

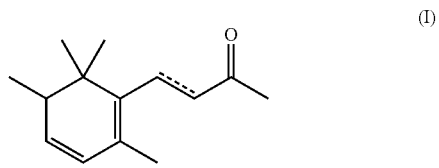

(I)

8 Claims, No Drawings

SAFFRON ODORANTS

TECHNICAL FIELD

The present invention relates to the field of perfumery. More particularly, it concerns a compound of formula

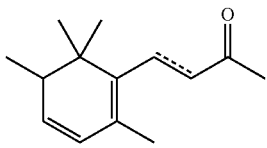

(I)

as defined herein below, as well as its use as perfuming ingredient. The present invention concerns also the invention's compound as part of a perfuming composition or of a perfuming consumer product.

PRIOR ART

To the best of our knowledge, none of the invention's compounds is known in the prior art. Perfuming ingredients having saffron odors are especially interesting for the perfumery industry.

The present invention's compounds are structurally related to the irones and ionones families, which are well known perfuming ingredients. All known irones and ionones used in perfumery have odors characterized by violette/orris or woody/fruity odors respectively, i.e. very different odors, and none of them has been reported or suggested as having even a slight saffron tonality (see Table 1 in the description).

Therefore, the odor properties of the present compounds are totally unexpected, especially considering that the structurally closest analogues having a saffron character are structurally very different (see Table 1 in the description).

DESCRIPTION OF THE INVENTION

We have now surprisingly discovered that a compound of formula

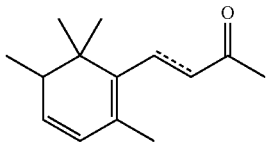

(I)

in the form of any one of its enantiomers or a mixture thereof, and wherein the dotted line represents a carbon-carbon single or double bond having predominantly a configuration E;

can be used as perfuming ingredient, for instance to impart odor notes of the saffron type together with aspects of the methylionone/orris type.

For the sake of clarity, by the expression "any one of its enantiomers", or the similar, it is meant the normal meaning understood by a person skilled in the art, i.e. that the invention's compound can be a pure enantiomer.

For the sake of clarity, by the expression "having predominantly a configuration E", or the similar, it is meant the normal meaning understood by a person skilled in the art, i.e. that the invention's compound can be in the form of a mixture of diasteroisomers of configuration E or Z wherein the E isomer account for at least 60% w/w of said mixture, more advantageously at least 80% or 90% w/w, percentage being relative to the total weight of said mixture.

For the sake of clarity, by the expression "wherein the dotted line represents a carbon-carbon single or double bond", or the similar, it is meant the normal meaning understood by a person skilled in the art, i.e. that the whole bonding (solid and dotted lines) between the carbon atoms connected by said dotted line, e.g. carbon 3 and 4, is a carbon-carbon single or double bond.

According to an embodiment of the invention, said compound (I) is 4-(2,5,6,6-tetramethylcyclohexa-1,3-dienyl)-but-3-en-2-one (i.e. the dotted line represents a carbon-carbon double bond). In particular, said 4-(2,5,6,6-tetramethylcyclohexa-1,3-dienyl)-but-3-en-2-one can be in the form of a mixture of (E) and (Z) isomers wherein the (E) isomer represents at least 60% w/w, or even at least 80% w/w, relative to the total weight of said mixture.

As specific example of the invention's compounds, one may cite, as non-limiting example, (E)-4-(2,5,6,6-tetramethylcyclohexa-1,3-dienyl)-but-3-en-2-one.

The compounds of formula (I) are also novel compounds, and therefore are also an object of the present invention.

Table 1 herein below reports the odor properties of the invention's compounds and, for comparison, the odor properties of prior art analogues and of other analogues not yet reported in the literature:

TABLE 1

Invention's compounds and their odor properties

| Compound structure and name | Odor notes |
|---|---|
| Present invention | |
| (E)-4-(2,5,6,6-tetramethylcyclohexa-1,3-dienyl)but-3-en-2-one | Predominantly saffron odor, with powdery nuance. Its odor is an unusual duality of saffron notes and an orris nuance which results in a spicy-oriental powdery character evoking saffron with a cosmetic twist (of the face powder type) |
| 4-(2,5,6,6-tetramethylcyclohexa-1,3-dienyl)butan-2-one | A balanced saffron and methylionone odor. Its odor is clearly saffron like, although the saffron note and the methyl ionone notes are of similar strength |
| Comparative examples | |
| 4-(2,6,6-trimethyl-5-methylene-3-cyclohexen-1-yl)-3-buten-2-one. Not disclosed in the prior art. | Orris, powdery, very natural. No saffron notes |

TABLE 1-continued

Invention's compounds and their odor properties

| Compound structure and name | Odor notes |
|---|---|
| 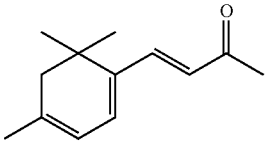<br>(E)-4-(4,6,6-trimethyl-1,3-cyclohexadien-1-yl)-3-buten-2-one | Metallic, powdery, woody<br>No saffron notes |

Examples of known Ionones and Irones

| Compound structure and name | Odor notes |
|---|---|
| 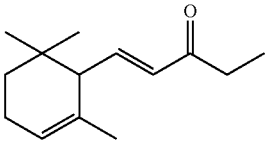<br>Methylionone alpha (see Arctander N° 2085) | Floral (orris/violet), sweet, odor with moderate tenacity<br>No saffron notes |
| 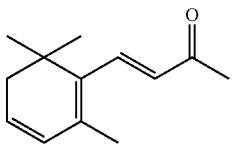<br>(E)-4-(2,6,6-trimethyl-1,3-cyclohexadien-1-yl)-3-buten-2-one (see JP 7121015 or U.S. Pat. No. 3,872,031) | Powdery, woody odor<br>No saffron notes |
| 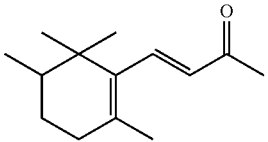<br>Beta irone (see Arctander N° 1785) | Similar to alpha irone but more powerful<br>No saffron notes |
| 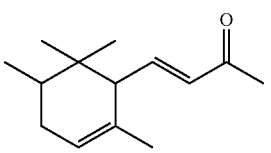<br>Alpha irone (see Arctander N° 1784) | Orris, violet-like, sweet and diffusive odor<br>No saffron notes |

Closest known analogues known to have a saffron note

| Compound structure and name | Odor notes |
|---|---|
| 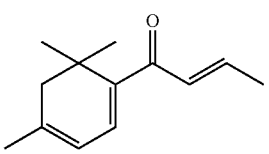<br>(E)-1-(4,6,6-trimethyl-1,3-cyclohexadien-1-yl)-2-buten-1-one (see EP 955290) | Mirabelle, damascenone, woody-saffron |

TABLE 1-continued

Invention's compounds and their odor properties

| Compound structure and name | Odor notes |
|---|---|
| 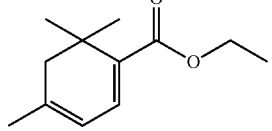<br>Ethyl 4,6,6-trimethyl-1,3-cyclohexadiene-1-carboxylate (see EP 1791934) | Saffron |
| 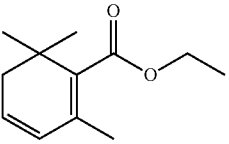<br>Ethylsafranate (origin: Givaudan SA, Switzerland) | Saffron |

When the odor of the invention's compounds is compared with that of the prior art ionones or irones, then the invention's compounds distinguish themselves by having a saffron character, the latter being totally absent in the prior art ionones or irones. Furthermore, the invention's compounds distinguish themselves from some prior art ionones or irones by lacking the woody notes so characteristic of some of said prior art compound(s).

The fact that the invention's compounds possess a saffron note which is dominant, or as powerful, compared to the other notes, renders said compounds and the ionones/irones suitable for different uses, i.e. to impart different organoleptic impressions. Indeed the closest analogues of the ionones and irones could not be used to impart saffron type notes or characters.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). Understood that the exact final hedonic effect, provided by said method or use, may depends on the precise dosage of the invention's compound and on the organoleptic properties of the initial perfumed composition, but anyway the addition of the compound will impart to the final product its typical character in the form of a note, touch or aspect depending on the dosage.

By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added.

Consequently, a perfuming consumer product which comprises:
i) as perfuming ingredient, at least one compound of formula (I), as defined above; and
ii) a perfumery consumer base; is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 20% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

The invention's compounds can be prepared according to a method as described in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

The compounds not part of the invention but prepared for comparatives purposes were obtained as follows:

4-(2,6,6-trimethyl-5-methylene-3-cyclohexen-1-yl)-3-buten-2-one

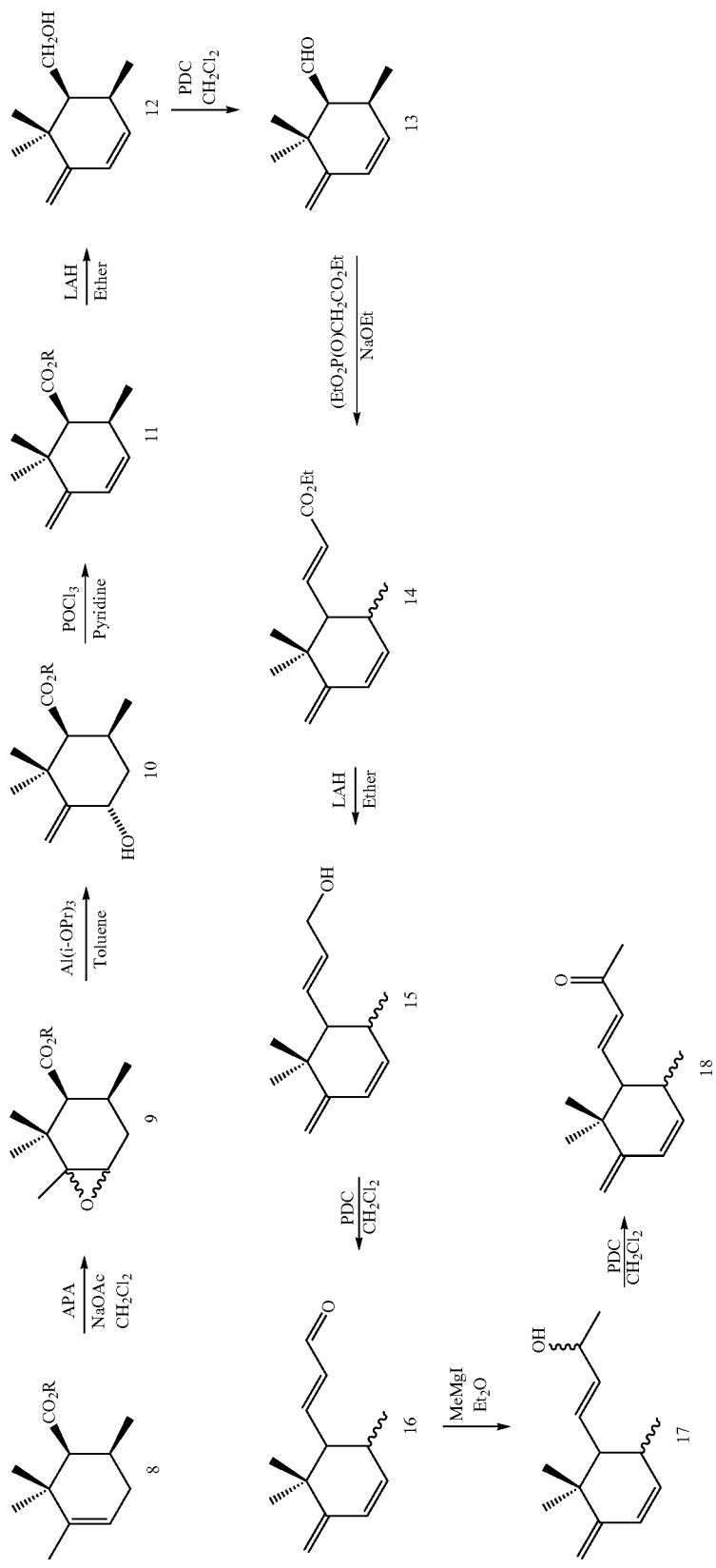

Reaction 8→9

Peracetic acid (40%, 2.71 g, 14.3 mmol) was added dropwise to a stirred suspension of 8 (3 g, 14.3 mmol) and NaOAc (0.7 g, 8.54 mmol) in CH$_2$Cl$_2$ (30 mL) at 0-5° C. The mixture was stirred for 2 hours at room temperature and diluted with water (50 ml). The organic phase was washed with Na$_2$CO$_3$ (10%) and brine, then distilled at 100° C./0.5 mbar to give 2.5 g of epoxide 9 as a 4:1 mixture of diastereomers (77% yield).

Reaction 9→10

A solution of 9 (2 g, 8.85 mmol) in 5 ml of toluene was added dropwise to a stirred solution of Al(i-OPr)$_3$ (0.35 g, 1.72 mmol) in toluene (20 ml) at 100° C., then refluxed for 1 hour. After cooling the mixture, it was washed with cold 10% H$_2$SO$_4$ and water, then chromatographed on silica to furnish 0.8 g of 94% alcohol 9 (40% yield).

Reaction 10→11

POCl$_3$ (2 g, 13 mmol) was added slowly to a stirred solution of 10 (1 g, 4.42 mmol) in pyridine (7 ml) at room temperature. After 20 hours, the reaction mixture was poured onto ice/water very slowly then extracted with ether, washed with 10% H$_2$SO$_4$, water, 5% NaHCO$_3$ and brine. Distillation (130° C., 0.5 mbar) furnished 11 (0.37 g, 65% purity=25% yield).

Reaction 11→12

Ester 11 was reduced with 0.5 molar equivalents of LiAlH$_4$, providing alcohol 12 in 88% yield.

Reaction 12→13

12 (1.88 g, 11.3 mmol) was oxidized with PDC (4.25 g, 11.3 mmol) to furnish aldehyde 13 (1.1 g, 59% yield).

Reaction 13→14

A solution of Na (0.08 g, 3.48 mmol) in EtOH (3 ml) was added to a mixture of 13 (0.4 g, 2.44 mmol), triethylphosphonoacetate (0.6 g, 2.68 mmol) and petroleum ether 30/50 (10 mL) and refluxed for 4 hours. After cooling, the reaction mixture was poured onto ice/HCl (10%), washed with brine, and distilled (150° C., 0.6 mbar) to furnish ester 14 (0.5 g, 88% yield) as a 1:1 mixture.

Reaction 14→15→16→17→18

A solution of ester 14 (0.49 g, 2.09 mmol) in ether (10 ml) was reduced with LiAlH$_4$ (0.08 g, 2.11 mmol) to give alcohol 15 in 89% yield. Oxidation of alcohol 15 with PDC furnished aldehyde 16 in 87% yield. Aldehyde 16 was then reacted with MeMgI in ether to give 0.27 g of alcohol 17 in 78% yield. Alcohol 17 was then reoxidized with PDC as previously to furnish 0.25 g of enone 18 (cis/trans=1:1). Prep GC furnished the pure isomers.

$^1$H NMR (cis-18): 0.91 (d, J=7.2, 3H), 1.03 (s, 3H), 1.13 (s, 3H), 2.07 (dd, J$_1$=4.8, J$_2$=10.7, 1H), 2.19 (s, 3H), 2.77 (br. s, 1H), 4.92 and 4.95 (two s, 2H), 5.44 (d, J=10, 1H), 6.02 (d, J=16, 1H), 6.11 (dd, J$_1$=2.8, J$_2$=10, 1H), 6.37 (dd, J$_1$=9, J$_2$=16, 1H)

$^{13}$C NMR (cis-18): 19.2, 26.6, 26.9, 28.8, 31, 37.7, 55.1, 111.7, 129, 131.3, 134.2, 148.1, 149.3, 198.6

$^1$H NMR (trans-18): 0.95 (d, J=7.2, 3H), 1.03 (s, 3H), 1.06 (s, 3H), 1.86 (tr., J=10.3, 1H), 2.28 (s, 3H), 4.82 and 4.97 (two s, 2H), 5.57 (d, J=10, 1H), 6.09 (dd, J$_1$=2.8, J$_2$=10, 1H), 6.1 (d, J=16, 1H), 6.68 (dd, J$_1$=10, J$_2$=16, 1H)

$^{13}$C NMR (trans-18): 20.1, 23.1, 26, 27.4, 32.4, 37.2, 55.4, 109.6, 128.3, 132.6, 134, 148.1, 151.9, 198.1

(E)-4-(4,6,6-trimethyl-1,3-cyclohexadien-1-yl)-3-buten-2-one

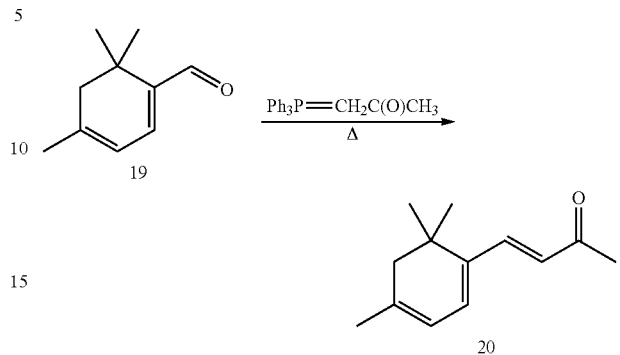

Aldehyde 19 (1.5 g, 10 mmol) and acetylmethylene-triphenylphosphorane (3.18 g, 10 mmol) in 30 ml of toluene was heated overnight in an autoclave to 180° C., then at 200° C. for 3 hours. The crude reaction mixture was chromatographed on silica to give 60 mg of pure 8.

$^1$H-NMR: 1.11 (s, 6H), 1.85 (s, 3H), 2.09 (s, 2H), 2.28 (s, 3H), 2.28 (s, 3H), 5.78 (dd, J$_1$=6, J$_2$=1, 1H), 6.31 (d, J=6, 1H), 6.39 (d, J=15, 1H), 7.21 (d, J=16, 1H)

$^{13}$C NMR: 23.8, 26.6, 27.4, 34.1, 45.8, 119, 125.7, 127.1, 139, 140.7, 143.1, 198.2

Example 1

Synthesis of Compounds of Formula (I)

Synthesis of (E)-4-(2,5,6,6-tetramethylcyclohexa-1,3-dienyl)but-3-en-2-one

Step 1

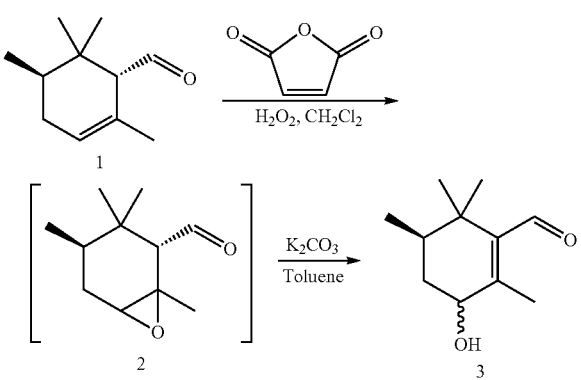

A 3-neck 1 l round bottom flask equipped with a condenser, thermometer and magnetic stir bar was charged with 115 g of pulverized maleic anhydride (1.17 mol), 150 g of aldehyde 1 (0.9 mol) and 435 ml of CH$_2$Cl$_2$. The solution was agitated under an atmosphere of N$_2$ and cooled to 10° C. with an ice water bath. Upon reaching the desired temperature, 64 g of 56% H$_2$O$_2$ (1.05 mol) was introduced with a syringe pump over a period of 1 hour. During the introduction, the reaction exothermed to 36° C. and solid precipitate was formed. The slurry was stirred for an additional 5 hours at room temperature to 96% conversion of aldehyde 1 into epoxide 2. The slurry was then diluted with approximately 500 ml of toluene and filtered using a Buchner funnel. The solid was discarded and the filtrate was concentrated on the rotovapor to remove most of the methylene chloride. The methylene chloride-free solution containing the crude epoxide 1 in toluene was then charged with 25 g of $K_2CO_3$ (0.18 mol) and brought to reflux. After 5 hours of reaction, epoxide 1 was completely converted to allylic alcohol 3 and the reaction mixture was cooled to room temperature and washed twice with 200 mL of water to neutral pH. After removing the toluene under reduced pressure with the rotovapor, 165 g of crude alcohol 3 was obtained. The latter was then distilled using a small vigreux column at 1-2 mbar, collecting 124 g of 98% pure allylic alcohol 1 at a vapor temperature of 109-115° C. Yield for 3 based on 1, 76%.

Step 2

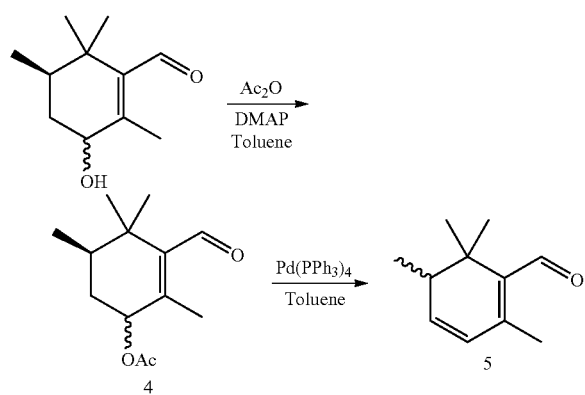

A 3-neck 250 ml round bottom flask equipped with a magnetic stir bar and reflux condenser was charged with 38 g of allylic alcohol 3 (0.22 mol), 0.53 g of N,N-dimethylamino pyridine (0.004 mol) and 58 g of toluene. The mixture was heated to 50° C. and then charged with 24 g of acetic anhydride (0.24 mol) over a 20 minute period. During the addition, the reaction exothermed to 60° C. before dropping to 55° C. at the end of the addition. Fifteen minutes after the end of the addition, GC analysis showed the complete conversion of starting material into acetate 4. The reaction mixture was cooled to room temperature and carefully poured into 288 g of saturated $NaHCO_3$. After neutralizing the acetic acid, the mixture was phase separated and the organic layer was concentrated under vacuum to obtain 42 g of crude acetate 4 at 96% purity and used for the next step without further purification.

A 3-neck 250 ml round bottom flask equipped with a magnetic stir bar and reflux condenser was charged with 28 g of crude acetate 4 (0.13 mol), 0.42 g of $Pd[P(C_6H_5)3]_4$ (0.00036 mol), 15.2 g of $Et_3N$ (0.15 mol) and 84 g of toluene. The solution was refluxed under $N_2$ for 1 hour to complete conversion. After cooling the reaction mixture to room temperature, it was washed with 10% $H_3PO_4$, followed by saturated $NaHCO_3$ and finally water to pH 7. After concentrating the organic layer, 21.5 g of crude aldehyde 5 was obtained at 89% purity. The latter was distilled with the kuegel-rohr to give 16.2 g of 95% pure aldehyde 5 (72% yield from 4, overall 68% yield from alcohol 3) along with 2.1 g of residue.

Step 3

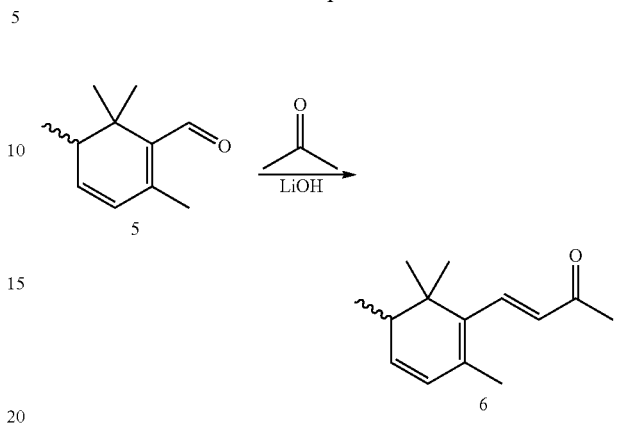

A 3-neck 100 ml round bottom flask equipped with a magnetic stir bar and reflux condenser was charged with 0.098 g of LiOH monohydrate (0.0023 mol), 68 g of acetone (1.17 mol) and 14 g of water. The mixture was brought to reflux then charged with 10 g of aldehyde 5 (96%, 0.058 mol) over a 1 hour period. The solution was refluxed for 9 hours to 97% conversion and then cooled to room temperature and neutralized with 1.8 g of 5% $H_3PO_4$. The reaction mixture was diluted with 80 g of heptane and phase separated. The aqueous phase was extracted twice with 15 g of heptane and the extracts combined with the original organic phase. Following concentration on the rotovapor, 14.3 g of crude concentrate was obtained, which was subsequently distilled on the kuegel-rohr to give 11.53 g of distillate containing ketone (E)-4-(2,5,6,6-tetramethylcyclohexa-1,3-dienyl)but-3-en-2-one at 87% purity (83% yield). The latter was further distilled on a 12.5 cm vigreux column to obtain 7.7 g of 94% pure material distilling at 77-78° C. at 0.5 mbar.

$^1$H-NMR: 0.94 (1H, d, J=7), 0.98 (3H, s), 1.08 (3H, s), 1.88 (3H, s), 2.06-2.15 (1H, m), 2.31 (3H, s), 5.72-5.76 (1H, dd, J=9, J=4), 5.80 (1H, doublet, J=9), 6.17 (1H, doublet, J=16), 7.25 (1H, doublet, J=16)

$^{13}$C NMR: 14.4, 20.71, 21.38, 26.67, 27.69, 37.70, 40.92, 128.18, 131.23, 131.82, 135.49, 135.99, 142.92, 198.73

Synthesis of 4-(2,5,6,6-tetramethylcyclohexa-1,3-dienyl)butan-2-one

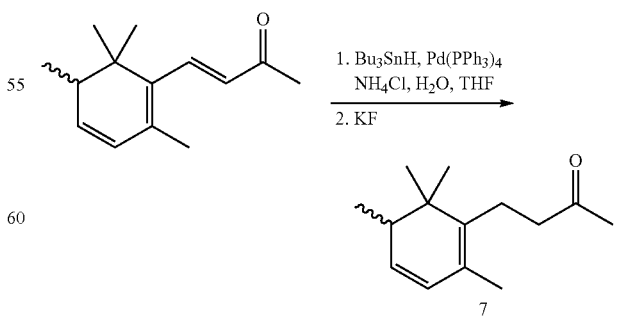

A 3-neck 50 ml round bottom flask equipped with a magnetic stir bar and reflux condenser was placed under $N_2$ and charged with 1 g of water (53 mmol), 2.2 g of NH₄Cl (41 mmol), 28 g of THF, 4 g of enone (E)-4-(2,5,6,6-tetramethylcyclohexa-1,3-dienyl)but-3-en-2-one (19.6 mmol) and 0.3 g of Pd(PPh₃)₄ (0.26 mmol). With stirring on, 5.7 g of SnBu₃H (19.6 mmol) was introduced over a 1 hour period at room temperature and stirred for another 4.5 hours until about 6% starting material remained. The reaction mixture was diluted with 100 ml of TAME, phase separated, washed with 50 ml of brine and concentrated on the rotovapor. The crude concentrate was rediluted with 50 g of EtOAc, poured into a 50 g solution of 50% KF and stirred for 4 hours. The mixture was phase separated and the organic layer was concentrated on the rotovapor to give 8 g of crude. The latter was column chromatographed on silica gel 60 (80:20 heptane/isopropyl ether) to give 2.6 g of 92% pure ketone 4-(2,5,6,6-tetramethylcyclohexa-1,3-dienyl)butan-2-one (61% yield).

¹H-NMR: 0.89 (3H, s), 0.91 (1H, d, J=8), 1.04 (3H, s), 1.69 (3H, s), 2.02 (1H, m), 2.17 (3H, s), 2.36 (2H, t, J=8), 2.51 (2H, t, J=8), 5.5 (1H, dd, J=9, J=4), 5.65 (1H, dd, J=10, J=1)

¹³C NMR: 14.1, 18.0, 20.1, 22.3, 26.1, 29.9, 37.8, 40.6, 43.6, 125, 127.6, 130.9, 137.5, 208.5

Example 2

Preparation of a Perfuming Composition

A perfuming composition, of the woody type, was prepared by admixing the following ingredients:

| Parts by weight | Ingredient |
|---|---|
| 60 | Benzylacetone |
| 20 | Cashmeran ®¹⁾ |
| 100 | Castoreum oil |
| 10 | Cetalox ®²⁾ |
| 350 | 10%** Civettine |
| 150 | Cypriol |
| 200 | (1'R,E)-2-Ethyl-4-(2',2',3'-trimethyl-3'-cyclopenten-1'-yl)-2-buten-1-ol³⁾ |
| 20 | 2-Methyl-4-(2,2,3-trimethyl-3-cyclopenten-1-yl)-4-penten-1-ol³⁾ |
| 110 | Gaiac |
| 80 | Methylionone Beta |
| 20 | Methylnaphthylcetone |
| 80 | 10%* Dextro 3-methyl-5-cyclopentadecen-1-one³⁾ |
| 20 | 10%* Myrrhone ®⁴⁾ |
| 20 | Safranal |
| 500 | Santal |
| 10 | 10%* Scatol |
| 1750 | |

*in dipropyleneglycol
**in ethyl citrate
¹⁾1,2,3,5,6,7-hexahydro-1,1,2,3,3-pentamethyl-4-indenone; origin: International Flavors & Fragrances, USA
²⁾dodecahydro-3a,6,6,9a-tetramethyl-naphtho[2,1-b]furan; origin: Firmenich SA, Geneva, Switzerland
³⁾origin: Firmenich SA, Geneva, Switzerland
⁴⁾4-(2,2,c-3,t-6-tetramethyl-R-1-cyclohexyl)-3-buten-2-one;; origin: Firmenich SA, Geneva, Switzerland The addition of 250 parts by weight of (E)-4-(2,5,6,6-tetramethylcyclohexa-1,3-dienyl)but-3-en-2-one to the above-described woody/agarwood composition reinforced the spicy-saffron aspect and conferred a unique warm powdery effect absent from the above composition.

The addition of the same amount of ionones or irones imparted totally different effect, devoid of any spicy reinforcement and unable to impart a warm powdery effect.

Example 3

Preparation of a Perfuming Composition

A perfuming composition for a soap, of the floral spicy type, was prepared by admixing the following ingredients:

| Parts by weight | Ingredient |
|---|---|
| 50 | Dimethyl benzyl carbinyl acetate |
| 20 | Styrallyl acetate |
| 20 | C 11 Undecylenic aldehyde |
| 100 | Hexylcinnamic aldehyde |
| 250 | Citronellol |
| 100 | 4-Cyclohexyl-2-methyl-2-butanol¹⁾ |
| 70 | Coumarine |
| 40 | Eugenol |
| 10 | 2-Methyl-4-(2,2,3-trimethyl-3-cyclopenten-1-yl)-4-penten-1-ol¹⁾ |
| 100 | Geraniol |
| 80 | Hedione ®²⁾ |
| 30 | Heliotropine |
| 40 | Helvetolide ®³⁾ |
| 40 | 10%* Isobutylquinoleine |
| 20 | Isoeugenol |
| 90 | Isoraldeine gamma |
| 150 | Lorysia ®⁴⁾ |
| 20 | 10%* Neobutenone ®⁵⁾ Alpha |
| 10 | Trans-1-(2,2,6-trimethyl-1-cyclohexyl)-3-hexanol¹⁾ |
| 40 | Patchouli oil |
| 150 | Phenethylol |
| 40 | Wardia ®⁶⁾ Rose |
| 50 | Rosinol |
| 100 | Amyl salicylate |
| 50 | Sclareolate ®⁷⁾ |
| 80 | Terpineol |
| 10 | Gamma undecalactone |
| 150 | Vertofix ®⁶⁾ Cœur |
| 40 | Ylang |
| 1950 | |

*in dipropyleneglycol
**in isopropyle myristate
¹⁾origin: Firmenich SA, Geneva, Switzerland
²⁾Methyl cis-dihydrojasmonate; origin: Firmenich SA, Geneva, Switzerland
³⁾(1S,1'R)-2-[1-(3',3'-dimethyl-1'-cyclohexyl)ethoxy]-2-methylpropyl propanoate; origin: Firmenich SA, Geneva, Switzerland
⁴⁾4-(1,1-dimethylethyl)-1-cyclohexyl acetate; origin: Firmenich SA, Geneva, Switzerland
⁵⁾1-(5,5-dimethyl-1-cyclohexen-1-yl)-4-penten-1-one; origin: Firmenich SA, Geneva, Switzerland
⁶⁾Compounded perfumery specialty; origin: Firmenich SA, Geneva, Switzerland
⁷⁾Propyl (S)-2-(1,1-dimethylpropoxy)propanoate; origin: Firmenich SA, Geneva, Switzerland
⁸⁾Methyl cedryl ketone; origin: International Flavors & Fragrances, USA The addition of 50 parts by weight of (E)-4-(2,5,6,6-tetramethylcyclohexa-1,3-dienyl)but-3-en-2-one to the above-described composition reinforced the spicy-aspect by imparting a saffron note which conferred to the new perfuming composition a new twist, almost curry type, and reinforced also powdery aspects of the initial composition.

The addition of the same amount of ionones or irones did not modify the spicy notes of the initial composition.

What is claimed is:

1. A method to confer, enhance, improve or modify the odor properties of a perfuming composition or of a perfumed article, which method comprises adding to said composition or article an effective amount of at least a compound of formula

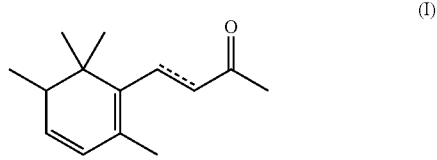

(I)

in the form of any one of its enantiomers or a mixture thereof, and wherein the bond between the two carbons connected by the dotted line being a single or double bond having predominantly a configuration E;

to impart odor notes of the saffron type together with aspects of the methylionone/orris type.

2. A method according to claim 1, wherein said compound is 4-(2,5,6,6-tetramethylcyclohexa-1,3-dienyl)-but-3-en-2-one.

3. A method according to claim 1, wherein said compound is (E)-4-(2,5,6,6-tetramethylcyclohexa-1,3-dienyl)-but-3-en-2-one.

4. A compound of formula

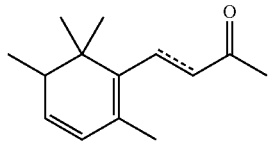

(I)

in the form of any one of its enantiomers or a mixture thereof, and wherein the bond between the two carbons connected by the dotted line being a single or double bond having predominantly a configuration E.

5. A perfuming composition comprising
 i) at least one compound of formula (I), as defined in claim 1;
 ii) at least one ingredient selected from the group consisting of a perfumery carrier and a perfumery base; and
 iii) optionally at least one perfumery adjuvant.

6. A perfuming consumer product comprising:
 i) at least one compound of formula (I), as defined in claim 1; and
 ii) a perfumery consumer base.

7. A perfuming consumer product according to claim 6, wherein said perfumery consumer base is a perfume, a fabric care product, a body-care product, an air care product or a home care product.

8. A perfuming consumer product according to claim 6, wherein said perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *